(12) United States Patent
Thomsen et al.

(10) Patent No.: US 6,845,272 B1
(45) Date of Patent: Jan. 18, 2005

(54) SKIN ELECTRODE

(75) Inventors: Steen Thomsen, Valby (DK); Brian Nielsen, Copenhagen (DK); Laila Busk Gothjælpsen, Jyllinge (DK)

(73) Assignee: Medicotest A/S, Olstkke (DK)

( * ) Notice: Subject to any disclaimer, the term of this patent is extended or adjusted under 35 U.S.C. 154(b) by 0 days.

(21) Appl. No.: 09/979,270

(22) PCT Filed: May 25, 1999

(86) PCT No.: PCT/DK99/00280

§ 371 (c)(1),
(2), (4) Date: Feb. 27, 2002

(87) PCT Pub. No.: WO00/71024

PCT Pub. Date: Nov. 30, 2000

(51) Int. Cl.$^7$ ................................................ A61N 1/04
(52) U.S. Cl. ........................................ 607/153; 607/142
(58) Field of Search .............................. 607/153, 397, 607/115, 142, 149; 600/372, 382, 386, 391, 392, 395, 396, 397

(56) References Cited

U.S. PATENT DOCUMENTS

| | | | |
|---|---|---|---|
| 3,841,312 A | 10/1974 | Corasanti | |
| 3,993,049 A | 11/1976 | Kater | |
| 4,300,575 A | 11/1981 | Wilson | |
| 4,352,359 A | 10/1982 | Larimore et al. | 128/640 |
| 4,365,634 A | 12/1982 | Bare et al. | |
| 4,377,170 A * | 3/1983 | Carim | 600/396 |
| 4,515,162 A | 5/1985 | Yamamoto et al. | 128/640 |
| 4,539,996 A | 9/1985 | Engel | |
| 4,554,924 A | 11/1985 | Engel | 128/640 |
| 4,583,551 A | 4/1986 | Pike | |
| 4,669,798 A | 6/1987 | Daum et al. | |
| 4,674,512 A | 6/1987 | Rolf | 128/640 |
| 4,757,817 A | 7/1988 | Healy | |
| 4,776,350 A | 10/1988 | Grossman et al. | |

(List continued on next page.)

FOREIGN PATENT DOCUMENTS

| | | |
|---|---|---|
| CA | 1326063 | 1/1994 |
| DE | 27 37 665 A1 | 3/1979 |
| DK | 169235 B1 | 9/1994 |
| EP | 0 052 968 A2 | 6/1982 |
| EP | 0 210 184 B1 | 4/1988 |
| EP | 0 322 852 A1 | 7/1989 |
| EP | 0 323 711 A1 | 7/1989 |
| EP | 0 449 800 A1 | 10/1991 |
| EP | 0 791 326 A3 | 8/1997 |
| EP | 0 791 326 A2 | 8/1997 |
| EP | 0 836 864 A2 | 4/1998 |
| EP | 0 965 358 A2 | 12/1999 |
| EP | 0 985 426 A3 | 3/2000 |
| EP | 0 985 426 A2 | 3/2000 |
| FR | 2 394 873 | 1/1979 |
| GB | 1 533 449 | 11/1978 |
| WO | WO 00/71024 A1 | 11/2000 |
| WO | WO 01/80943 A1 | 11/2001 |
| WO | WO 01/91637 A1 | 12/2001 |
| WO | WO 02/05712 A1 | 1/2002 |
| WO | WO 02/07597 A1 | 1/2002 |

OTHER PUBLICATIONS

U.S. Appl. No. 10/258,807, Nielsen et al., filed Oct. 28, 2002, 3 pages.
U.S. Appl. No. 10/296,708, Neilsen et al., filed Nov. 27, 2002, 5 pages.
U.S. Appl. No. 10/333,325, Brian Nielsen, filed Jan. 17, 2003, entitled "A Skin Electrode with a By–Pass Element," 24 pages.

(List continued on next page.)

*Primary Examiner*—George R. Evanisko
(74) *Attorney, Agent, or Firm*—Sterne Kessler Goldstein & Fox PLLC

(57) ABSTRACT

An electrode for establishing electrical contact with the skin is disclosed, said electrode having a low impedance and comprising an electrically conductive metallic layer (4) and an electrically conductive gel (12) attached to said metallic layer, wherein the pH of the electrically conductive gel (12) is chosen so as to provide a corrosion of the metallic layer (4).

18 Claims, 2 Drawing Sheets

U.S. PATENT DOCUMENTS

| | | | |
|---|---|---|---|
| 4,834,103 A | | 5/1989 | Heath .................. 128/798 |
| 4,838,273 A | | 6/1989 | Cartmell |
| 4,846,185 A | * | 7/1989 | Carim .................. 600/391 |
| 4,848,348 A | | 7/1989 | Craighead ............ 128/639 |
| 4,852,585 A | | 8/1989 | Heath .................. 128/798 |
| 4,895,169 A | | 1/1990 | Heath .................. 128/798 |
| 4,957,453 A | | 9/1990 | Owen |
| 4,989,607 A | | 2/1991 | Keusch et al. ........ 128/640 |
| 5,195,908 A | | 3/1993 | Yamamoto et al. |
| 5,197,472 A | | 3/1993 | DiSabito |
| 5,203,330 A | | 4/1993 | Schaefer et al. |
| 5,250,022 A | * | 10/1993 | Chien et al. ............ 604/20 |
| 5,250,023 A | * | 10/1993 | Lee et al. ............... 604/20 |
| 5,264,249 A | | 11/1993 | Perrault et al. ........ 427/327 |
| 5,299,954 A | | 4/1994 | Ishii |
| 5,330,526 A | | 7/1994 | Fincke et al. .......... 607/142 |
| 5,355,883 A | | 10/1994 | Ascher |
| D366,317 S | | 1/1996 | Axelgaard |
| 5,520,683 A | * | 5/1996 | Subramaniam et al. ..... 607/149 |
| 5,611,709 A | | 3/1997 | McAnulty |
| 5,730,126 A | | 3/1998 | Kantner et al. |
| D423,673 S | | 4/2000 | Bass.o slashed.e |
| D423,674 S | | 4/2000 | Bass.o slashed.e |
| D457,634 S | | 5/2002 | Rouns et al. |
| D478,173 S | | 8/2003 | Nielsen |
| 2003/0130714 A1 | | 7/2003 | Nielsen et al. |
| 2003/0153822 A1 | | 8/2003 | Nielsen et al. |

OTHER PUBLICATIONS

U.S. Appl. No. 10/333,325, Brian Nielsen, filed Jan. 17, 2003, as amended Jan. 17, 2003, 2 pages.

U.S. Appl. No. 10/333,780, Bassoe et al., filed Jan. 24, 2003, entitled "An Electromedical Electrode with a Snap Connecting Means," 20 pages.

U.S. Appl. No. 10/333,780, Bassoe et al., filed Jan. 24, 2003, as amended Jan. 24, 2003, 4 pages.

Dialog File 351, Accession No. 1979–C0411B, Derwent WPI English language abstract for DE 27 37 665, Derwent Information Ltd, 1 page.

Dialog File 348, European Patents English language abstract for EP 449 800, European Patent Office, 2 pages.

English Language Translation of French Patent No. 2 394 873, Internationalt Patent–Bureau, Jan. 4, 2002,

* cited by examiner

SKIN ELECTRODE

CROSS-REFERENCE TO RELATED APPLICATIONS

This application is the § 371 U.S. National Phase Entry of International Application No. PCT/DK99/00280, filed May 25, 1999 and published under PCT Article 21(2) in English, which is incorporated herein by reference.

TECHNICAL FIELD

The present invention relates to an electrode for establishing electrical contact with the skin. More specifically, this invention relates to physiological electrodes by means of which a plurality of physiological functions may be monitored or stimulated, either individually or in combination, through a single electrode set.

BACKGROUND ART

Electrodes establishing electrical contact with the skin are used for the administration of electrical signals to the body as well as collecting electrical signals generated in the body.

Electrical signals may be administered to the body of a patient through skin electrodes for a variety of reasons, including the treatment of fibrillation by administering an electric shock, treatment of pain and promotion of healing. The electric shock counteracts atrial or ventricular fibrillation of the heart and, if the treatment succeeds, makes the rhythm of the heart revert to the normal mode.

Electric signals generated in the body may be collected by skin electrodes and monitored on a suitable monitoring device. In particular, the electrical signals of the heart may be monitored on a electrocardiogram (in the following abbreviated as ECG) to monitor the operation of the heart.

Skin electrodes have to meet a plurality of requirements to be suitable for supplying or measuring electrical signals, e.g. the skin electrodes must be sufficiently flexible to conform with the patient's body to secure a sufficient contact area, and to display satisfactory adhesion and electrical contact with the patient's body when the electrodes are placed properly. A special requirement consists in the presence of a low impedance to ensure a good transmission of electric energy and a low polarization of the electrode.

If a skin electrode shows a too small ability to transmit energy, the risk exists that the skin of the patient will get burned during defibrillation. Furthermore, during long-term monitoring of ECG, a tendency of the baseline to drift is observed which is believed to be caused by a high D.C. offset. The D.C. offset is a minute current produced by the electrochemical composition of the electrode itself and is influenced by the impedance. The drift decreases the accuracy of the measurements.

A set of skin electrodes may serve the dual purpose of administering an electric shock to a patient liable to fibrillation and monitoring the ECG. It is crucial for the success of the treatment to obtain an ECG as soon as possible after the administration of the electric shock in order to evaluate the effect of the shock treatment. If the electrodes show a high D.C. offset, the ECG trace will be lost for a period lasting from a few seconds to more than a minute after the application of a defibrillation signal because of polarization of the electrodes.

Several prior art documents address the problem of reducing the impedance or increasing the conductivity. In U.S. Pat. Nos. 4,895,169, 4,834,103 and 4,852,585 it is suggested to use an electrode element of tin and stannous chloride. The stannous chloride may be directly applied to the tin surface, e.g. by spraying a thin layer thereon, or it may be located in the conductive medium.

In U.S. Pat. No. 4,352,359, an electrode is disclosed wherein the impedance is lowered by the presence of a synthetic polymer containing at least 5 mole percent of monomer units containing a salt of a carboxylic acid. In EP 0 836 864, it is suggested to use a conductive hydrogel adhesive containing an electrolyte distributed over the foil plate to increase the conductivity, potassium bromide being the preferred electrolyte. In U.S. Pat. No. 4,989,607 it is suggested to use a highly conductive hydrogel comprising a cohesive uniform mixture of poly(vinyl pyrrolidone), a viscosity-enhancing hydrophillic polymer and an electrolyte.

In the prior art, it is often indicated that the corrosion of the metal foil plate is undesired because it reduces the shelf-life of the skin electrode and the compliance with the skin of the patient, cf. for instance U.S. Pat. Nos. 4,834,103, 4,852,585, 4,895,169, 4,674,512 and Danish Patent No 169,235.

The interface between the electrically conductive gel and the metallic layer is of major importance to the conductivity. An effective electrically coupling of the two layers will permit rapid depolarization of the electrode after defibrillation. If the coupling is satisfactory, the electrode will exhibit a relative low and constant D.C. offset.

To be a satisfactory high-performance electrode, the impedance should not vary considerably throughout the used range of frequencies. Especially for ECG applications, low impedances are of importance also at low frequencies. For a typical electrode in the market, e.g. comprising a tin foil coated with a hydrogel containing sodium chloride as an electrolyte, the impedance will rise rapidly when the electrode is subjected to an applied alternating current as the frequency of that current decreases (say 30 kHz to 10 Hz)

The problem of providing a satisfactory electrically coupling between the electrically conductive metallic layer and the electrically conductive gel is attended to herein. Especially, it is the objective of the present invention to reduce the impedance and the D.C. offset to an acceptable low level. Furthermore, it is the objective to reduce the impedance to an acceptable low level at high as well as low frequencies, making the present electrode suitable for a combined use for defibrillation and ECG.

DISCLOSURE OF THE INVENTION

According to the present invention an electrode for establishing electrical contact with the skin is provided, comprising an electrically conductive metallic layer and an electrically conductive gel attached to said metallic layer, wherein the pH of the electrically conductive gel is chosen so as to provide a corrosion of the metallic layer.

The electrically conductive gel may provide an acidic or an alkaline corrosion of the metallic layer. The acid or alkaline electrically conductive gel, respectively, may be provided in any suitable way. In one embodiment a mineral or organic acid or base, that provides for the eventually obtained pH, is added to the gel during the preparation thereof. Examples of mineral or organic acids that may be used are hydrochloric acid, sulphuric acid, nitric acid, phosphorus acid, acetic acid, formic acid, benzoic acid, sulfonic acid. Examples of mineral or organic alkaline substances that may be used are ammonia, potassium hydroxide, sodium hydroxide, calcium hydroxide, pyridine, aniline. In another embodiment, which is explained in more detail later in this description, the polymers of the gel structure itself contains acid or alkaline groups. In a third embodiment of the invention, a combination of the two preceding embodiments are used, i.e. the gel contains a mineral or organic acid or base added during the preparation as well as polymers carrying acid or alkaline groups.

Preferably, the gel provides an acidic corrosion. The chosen pH of the electrically conductive gel depends on the selected metallic layer and may be determined by the person skilled in the art through routine experiments.

The pH of the electrically conductive gel is preferably between 0 and 4, more preferred between 1 and 3. The selected pH is a trade-off between skin compatibility and sufficient corrosion of the metallic layer. Therefore, the preferred metals for the metallic layer is selected among metals having a high sensitivity to acid or base. Preferred metals include tin, aluminium, zinc and lead and any combination thereof. Tin is the most preferred metal for the metallic layer. The purity of the used metal is usually high. Preferably, the purity is 99% by weight or more. The thickness of the metallic layer is not of particular importance to the present invention. A thickness of 0.05 mm has proved to be useful.

Without the intention of limiting the invention to a specific theory, it is believed that the chemical attack of the metallic layer provides a diminished impedance at the interface between the metallic layer and the acidic gel. The chemical attack will result in the creation of pits in the surface of the metallic layer, thus increasing the surface area so that the electrical contact between the gel and the metallic layer is improved. It is also believed that the generation of a relatively high concentration of metallic ions at the interface contributes to the availability of current carriers when a current is impressed, resulting in a reduced tendency to build-up charge, i.e. to serve as a capacitor.

A number of various electrically conductive gels wellknown to the person skilled in the art may be used in the electrode according to the invention. Preferred gels are prepared of hydrophillic polymers. In the following, gels prepared of hydrophillic polymers will be termed hydrogels. Hydrogels comprise an amount of water, which increases the skin compatibility and lower the electrical resistance.

The hydrophillic polymer may for instance be selected from the group consisting of polyacrylate, polymethacrylate, polyacrylamide, poly(vinyl alcohol), poly(ethylene oxide), poly(ethylene imine), carboxy-methylcellulose, methylcellulose, poly(acrylamide sulphonic acid), polyacrylonitril, poly(vinyl-pyrrolidone), agar, dextran, dextrin, carrageenan, xanthan, and guar.

Preferred polymers comprise ionizable groups. If the corrosion of the metallic layer is performed in an acidic environment, it is preferred that the ionizable groups are acid groups, such as carboxylic, sulphonic or nitric groups. In acidic environments such groups will predominantly be anionic and may thus be capable of transferring a cation carrying a charge between the skin of the patient and the metallic layer. A preferred polymer is polyacrylate or polymethacrylate, or a copolymer containing acrylic acid or methacrylic acid as one of its monomers.

A polyacrylate at low pH may contain a fairly large amount of water providing a sticky gel with an ability to penetrate the small pores of the skin. In a preferred embodiment of the invention the content of water in the gel is above 50% by weight, more preferred above 70% by weight, when the pH of the gel is between 1 and 3. The satisfactory coupling between the gel and the surface of the skin of a patient results in a low skin impedance. Furthermore, the electrode adheres well to the skin of the patient and remains in position during operation even if tension is applied thereto. The satisfactory coupling also ensures a high energy transfer resulting in substantially no burning of the skin.

If the corrosion of the metallic layer is provided in an alkaline environment, it is preferred that the ionizable groups of the polymeric structure are basic groups, such as amine, imine, or amide groups. In alkaline environments, such groups will predominantly be cationic and may thus be capable of carrying a free anion in the gel.

Even though some ions are etched from the metallic layer and may serve to transfer an electrical charge from the metallic layer to the skin surface, it may be desired to add further ions to improve the conductivity of the gel. The ions may be added as an ionizable salt. In principle, any ions having the ability to move in the gel may be used. However, preferred ionizable salts are KCl, KBr, NaCl, AgCl or $SnCl_2$.

Preferably, the face of the metallic layer opposite to the face attached to the electrically conductive gel has a suitable insulating cover in order to reduce the risk that the operator will get shocked too during treatment of defibrillation. The insulating cover is preferably prepared of a polymeric material such as polyolefine, e.g. polyethylene or polypropylene.

The metallic layer may be connected to instruments or devices that are utilized in connection with skin electrodes in any suitable way. It is, however, preferred that the electrically conductive metallic layer is connected with a point adapted to mate with a corresponding portion of a connector, because, especially in an emergency situation, the electrodes may easily be connected to the devices or an instrument. Furthermore, the presence of a point adapted to mate with the corresponding parts of a connector of an instrument or device allows the electrode to be a disposable article. Thus, the electrode may be adapted for single use and may be disposed of in any suitable way.

Whereas the electrically conductive gel used in the present invention is preferably a hydrogel having the ability to adhere to the skin of the patient, it may be preferred to cover the face opposing the face in contact with the metallic layer by a second or further electrically conductive skin adhering layer(s) having a pH more compatible with the skin of the patient. The pH of the second gel layer is preferably 5–9.

The corrosion of the metallic layer normally progresses, also during the storage of the electrode, and the effect may be a reduced shelf-life. An improved shelf-life may, however, be obtained if the metallic layer is connected to a sacrificial electrode during storage. Prior to the use of the electrode according to the invention, the connection between the metallic layer and the sacrificial electrode is interrupted. The material for the sacrificial electrode may be selected among any metals having a higher tendency to corrode than the metal selected for the metallic layer of the electrode. The sacrificial electrode may also be a pole of a battery.

The electrode according to the present invention may be used for a variety of applications, including monitoring, stimulation, therapeutical and surgical applications. The monitoring applications include any measurement of the condition of the muscles or nerves of the human or animal body. Specific examples for the use of the electrode according to the present invention for monitoring applications are ECG, EMG (electromyography) and EEG (electroencephalography).

The stimulating applications include any method for stimulation of the muscles or nerves of the human or animal body. Specific examples of the use of the electrode according to the present invention for stimulating applications are for defibrillation, pacing and pain relief.

Examples of therapeutical applications of the electrode according to the present invention are for electrotherapy of muscles and nerves.

The electrode according to the present invention may also be used for surgical applications as grounding plate. A grounding plate is used in a special surgical technique wherein the tissue of the patient is cut with a needle supplied with a high voltage. When the needle supplied with the high voltage comes into contact with the skin heat will be developed and the tissue may be cut. The grounding plate is used to close the electrical circuit. To avoid burning the grounding plate usually has a fairly large size.

DETAILED DESCRIPTION

Figure 1:
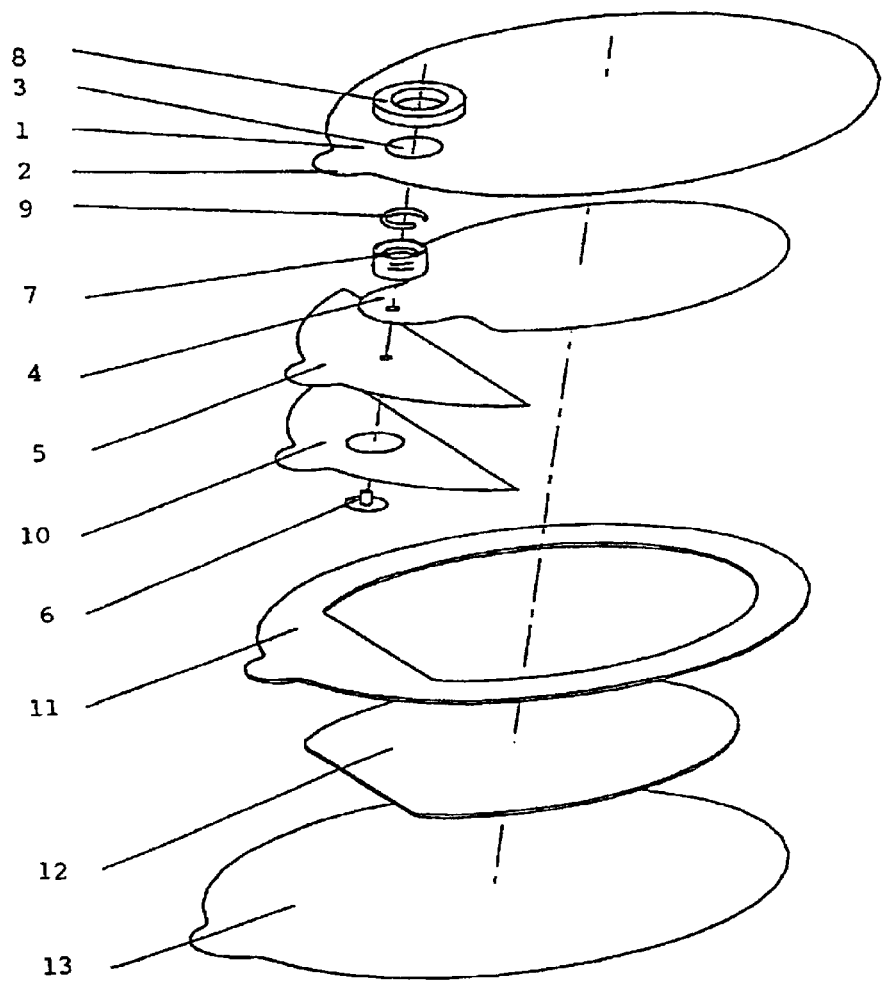
FIG. 1 is a split view of a multi functional defibrillation electrode according to a preferred embodiment of the present invention.

FIG. 1 shows a split assembly view of an electrode according to a preferred embodiment of the invention. The embodiment shown in FIG. 1 includes an electrically insulating backing or substrate 1. The substrate 1 has an oval overall shape and an ear 2 attached to the circumference thereof. In addition, the substrate 1 comprises an aperture 3 near the ear 2. A metallic foil plate 4 is centred attached to the substrate 1. On the face of the metallic foil plate opposite the substrate, a relief film 5 is placed in the area in the vicinity of the point. A minor hole is provided in the relief film as well as the foil plate through which a rivet 6 is provided. The rivet 6 fastens a cup 7 to the foil plate 4 to provide an effective electrical contact. Inside the cup, a snap ring 8 is placed to allow for easy and fast connection. The cup 7 protrudes through the aperture 3. Around the cup, an insulating space 9 of a annular foam material is attached. A double sided adhesive tape 10 is adhering to the relief film 5 on the one side and to a frame 11 on the other. The area delimited by the frame and the foil plate is filled with an electrically conductive gel 12. The surface of the gel 12 opposite the foil plate 4 is provided with a release liner.

Prior to the use of the skin electrode according to the embodiment shown in FIG. 1, the release liner is removed and the surface of the gel is brought into contact with the skin of a patient. The skin adhering ability of the gel secures that the electrode remains in position.

Figure 2:
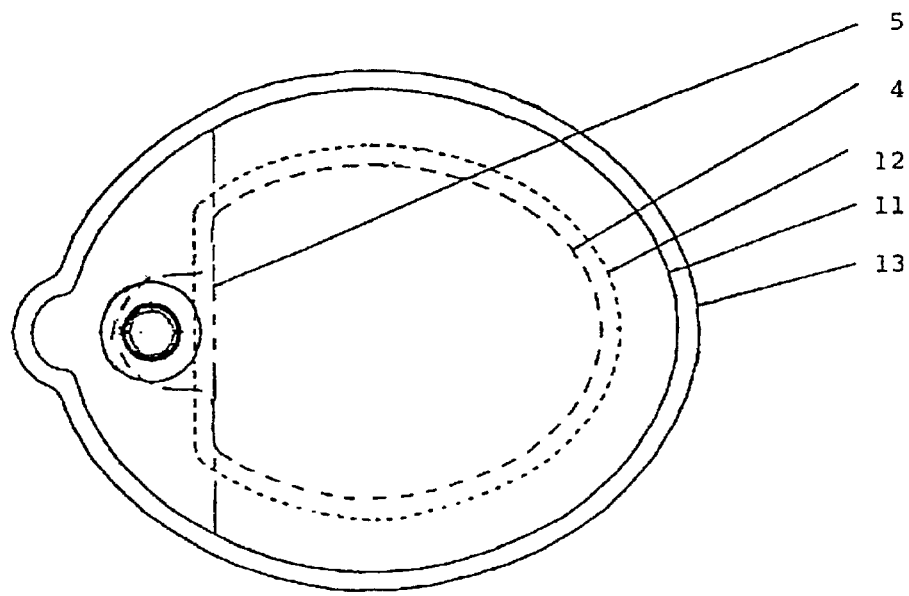
FIG. 2 is the electrode according to the embodiment shown in FIG. 1 shown from the top.

FIG. 2 shows the electrode according to the embodiment of FIG. 1 seen from above. The dashed line closest to the centre of the electrode demarcates the foil plate 4. Around the foil plate, the gel 12 is shown by the minor dashed line. The gel extends beyond the circumference of the foil plate, except in the vicinity of the point, in order to secure a satisfactory administration of electricity to the patient and a corrosion of the foil plate in its entirety, except near the point. The frame 11 surrounds the gel and is in contact with the release liner 13.

Figure 3:
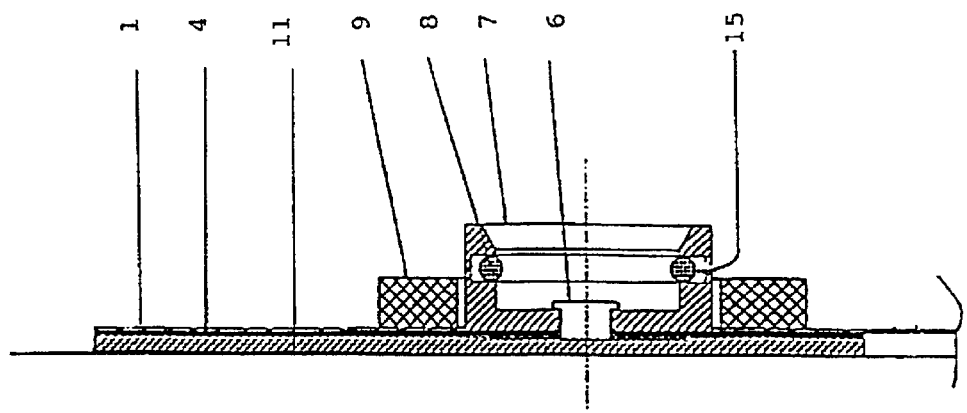
FIG. 3 is a lateral sectional view of a point connected to the foil plate.

FIG. 3 shows an enlarged lateral sectional view of a point. The cup 7 is placed on the foil plate 4 and fastened by means of a rivet 6. The cup 7 has a groove 15 formed therein containing a snap ring 8. The snap ring may be made of stainless steel or another resilient material. Part of the ring is missing to enable contraction and expansion. Upon attachment of a connector, snap ring 8 expands and exerts an inward force securing the connector within the cup 7. Around the point, the insulating spacer 9 is provided. The insulating spacer is fastened to the substrate and, during operation, it secures the medical staff not getting shocked.

A skin electrode may be prepared by casting an uncured precursor for the gel in a matrix defined by the frame and the foil plate. The precursor is subsequently irradiated by UV light to cure the gel. A release liner may then be attached to the surface of the gel and the frame. The matrix may be prepared by attaching the foil plate to the substrate and attaching the frame to the substrate as well as mounting the point.

Alternatively, the gel precursor may be cast in the desired thickness on a liner optionally covered by a tissue and subsequently cured by UV radiation. The gel plate may subsequently be assembled with the matrix to produce an electrode according to the invention. The liner may be provided with a top liner, if desired.

EXAMPLE

A precursor for the electrically conductive gel was prepared by mixing 7,670 g water, 25 g KCl and 2,250 g acrylic acid during agitation. The agitation continued until all the KCl was dissolved. Subsequently, 24 g triethyleneglucol dimethacrylate and Darocure 1173 was added and the mixture was agitated in the dark for further 30 min. The precursor may then be cured by exposure to ultra-violet light. The pH value of the cured gel was 2.

Skin electrodes were prepared by casting the precursor for the gel in a thickness of 1 mm on a liner covered by a tissue and subsequently curing by UV radiation. The gel plate was subsequently assembled with a matrix. The matrix was prepared by adhering a tin foil plate to the substrate and subsequently attaching the frame to the substrate as well as mounting the point. Finally, the liner was covered with a top liner.

Multi functional defibrillation electrodes prepared as depicted above were tested in accordance with the following electrical characteristics.

AC Small Signal Impedance

Two electrodes were connected gel to gel. The impedance, measured at 10 Hz and 30 kHz at a level of impressed current not exceeding 100 mA, was 0.95 Ω and 0,81 Ω, respectively.

AC Large Signal Impedance

The impedance of a pair of electrodes connected gel to gel in series with a 50 Ω load was measured at 360 J to 0,9 Ω.

DC Offset Voltage

A pair of electrodes were connected gel to gel. After a one minute stabilisation period, the offset voltage was 4 mV.

Defibrillation Overload Recovery

The potential of a pair of electrodes connected to a 50 Ω test load and subjected to 10 shocks at 360 J at a one minute interval, was measured to 15 mV at 4 s and 10 mV at 60 s after the last shock administration. In addition, the DC offset drift was measured to 0.1 mV/s after 10 s.

Combined Offset Instability and Internal Noise

After a one minute stabilization period, a pair of electrodes connected gel to gel generated a maximum voltage of 7 µV peak to peak in a pass band of 0.5 to 40 Hz, for a period of 5 minutes following the stabilization period.

Thorax Impedance

The electrodes according to the invention were applied to a group of 48 test candidates of varying age and gender. The impedance was measured at two frequencies using a sinusoidal current having a rms. value <50 $\mu$A. At a frequency of 2 kHz, the mean impedance was 218 $\Omega$ and at a frequency of 5 Hz, 12.8 $\Omega$.

Pacing

A pair of electrodes according to the invention was connected gel-to-gel in series with a 50 $\Omega$ test load and subjected to 60 minutes of pacing at a current of 200 mA and a rate of 180 pulses per minute. Following the pacing, the values, calculated as the average of 4 pairs of electrodes, of the individual tests were:

| | |
|---|---|
| AC small impedance | 10 Hz: 1.6$\Omega$ |
| | 30 kHz: 1.1$\Omega$ |
| AC large signal impedance | 1.5$\Omega$ |
| DC offset voltage | 90 mV |
| Defibrillation overload recovery | 4 s: 55 mV |
| | 60 s: 50 mV |
| | Drift(10 s): 0.1 mV/s |
| Combined offset instability and internal noise | 8 $\mu$V |

The data show that the impedance is low both at small and large signals. Furthermore, the frequency variations have little effect on the impedance, which suggest that the impedance is low.

The data for defibrillation overload recovery show that ECG may be measured almost immediately after the administration of the defibrillation shock. The electrodes according to the present invention thus allow the attending physician to monitor the effect of the defibrillation shock treatment immediately after administering the electric shock.

The data for pacing show a very low drift (0.1 mv/s) indicating that only a minor amount of charge is polarized in the electrodes. Thus, the tendency to deteriorate during long term pacing is not as pronounced as usually observed.

The electrode may be described as essentially non-polarizable having a virtually ohmic and a very low capacitive transfer of energy.

What is claimed is:

1. A defibrillation or electrocardiogram electrode for establishing electrical contact with the skin, said electrode comprising an electrically conductive metallic layer having a high sensitivity to acid and an electrically conductive gel attached to said metallic layer, thereby providing an interface between said gel and said metallic layer, wherein said electrically conductive gel has a pH between 1 and 3 so as to provide corrosion of said metallic layer, wherein a high concentration of ions are etched from said metallic layer, generating a concentration of metallic ions at the interface between the gel and said metallic layer, said concentration of metallic ions contributing to the availability of current carriers when a current is impressed on the electrode, and wherein said defibrillation or electrocardiogram electrode is adapted for administering an electric shock to a patient or monitoring the electrocardiogram of said patient when connected to a defibrillator or an electrocardiogram apparatus.

2. An electrode according to claim 1, wherein the electrically conductive metallic layer is selected from the group consisting of tin, aluminium, zinc and lead.

3. An electrode according to claim 2, wherein said electrically conductive metallic layer comprises tin.

4. An electrode according to claim 3, wherein said electrically conductive metallic layer consists of tin having a purity of 99% by weight or more.

5. An electrode according to claim 1, wherein said electrically conductive gel is a hydrogel.

6. An electrode according to claim 1, wherein said electrically conductive gel comprises a polymer containing ionizable groups in a polymer structure.

7. An electrode according to claim 6, wherein said electrically conductive gel comprises a polymer containing acid groups.

8. An electrode according to claim 7, wherein said electrically conductive gel comprises a copolymer of acrylic acid or a homopolymer of acrylic acid.

9. An electrode according to claim 1, wherein said electrically conductive gel comprises an ionized salt homogeneously distributed therein.

10. An electrode according to claim 9, wherein said salt is selected from the group consisting of KCl, KBr, NaCl, AgCl and SnCl$_2$.

11. An electrode according to claim 1, wherein said electrically conductive metallic layer on the face opposite the face attached to the electrically conductive gel is covered by an electrically insulating cover.

12. An electrode according to claim 1, wherein said electrically conductive metallic layer is connected to a point adapted to mate with a corresponding portion of a connector.

13. An electrode according to claim 1, wherein said electrically conductive gel on the face opposite the metallic layer is covered by one or more electrically conductive gel layers.

14. An electrode according to claim 13, wherein said one or more electrically conductive gel layers has a pH of 5–9.

15. An electrode according to claim 1, wherein said electrically conductive gel contains above 50 percent by weight of water.

16. An electrode according to claim 1, wherein said electrically conductive gel contains above 70 percent by weight of water.

17. A defibrillation and electrocardiogram electrode for establishing electrical contact with the skin, said electrode comprising an electrically conductive metallic layer having a high sensitivity to acid and an electrically conductive gel attached to said metallic layer, thereby providing an interface between said gel and said metallic layer, wherein said electrically conductive gel has a pH between 1 and 3 so as to provide corrosion of said metallic layer, wherein a high concentration of ions are etched from said metallic layer, generating a concentration of metallic ions at the interface between the gel and said metallic layer, said concentration of metallic ions contributing to the availability of current carriers when a current is impressed on the electrode, wherein said electrode is adapted to be a combined defibrillation and electrocardiogram electrode, and wherein said combined defibrillation and electrocardiogram electrode is adapted for administering an electric shock to a patient and monitoring the electrocardiogram of said patient when connected to a defibrillator and an electrocardiogram apparatus.

18. A method of improving the shelf-life of the electrode according claim 1 or and 17 wherein, during storage, the metallic layer is connected to a sacrificial electrode.

* * * * *